(12) United States Patent
Horsley

(10) Patent No.: US 9,095,744 B2
(45) Date of Patent: *Aug. 4, 2015

(54) MEDICAL EXERCISE DEVICE

(71) Applicant: Caryn M. Horsley, Bellport, NY (US)

(72) Inventor: Caryn M. Horsley, Bellport, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/909,623

(22) Filed: Jun. 4, 2013

(65) Prior Publication Data

US 2013/0324381 A1    Dec. 5, 2013

Related U.S. Application Data

(63) Continuation-in-part of application No. 13/488,333, filed on Jun. 4, 2012.

(51) Int. Cl.
| | | |
|---|---|---|
| *A63B 21/02* | (2006.01) |
| *A63B 21/05* | (2006.01) |
| *A63B 21/00* | (2006.01) |
| *A61F 6/06* | (2006.01) |

(Continued)

(52) U.S. Cl.
CPC ............... *A63B 23/20* (2013.01); *A63B 21/026* (2013.01); *A61F 6/06* (2013.01); *A63B 21/02* (2013.01); *A63B 21/05* (2013.01); *A63B 21/055* (2013.01); *A63B 21/0552* (2013.01); *A63B 21/0555* (2013.01)

(58) Field of Classification Search
CPC ................... A61B 2017/00309; A61F 2/2445; A61F 5/08; A61F 2/2442; A61F 2/2448; A63B 21/02; A63B 21/026; A63B 21/028; A63B 21/04; A63B 21/0407; A63B 21/0414; A63B 21/0421; A63B 21/0428; A63B 21/0435; A63B 21/0442; A63B 21/045; A63B 21/0455; A63B 21/05; A63B 21/055; A63B 21/0552; A63B 21/0555; A63B 23/20
USPC ........... 482/92, 121–122, 124, 128–139, 148, 482/907; 128/119.1, 830, 834–836, 128/839–840, 842, 884–885, 897–898, 128/DIG. 25; 600/29–32, 37; 601/23, 45; 604/104–106, 330–331, 385.17; 606/151–158, 191, 193, 196–198, 606/201–204.45, 235
See application file for complete search history.

(56) References Cited

U.S. PATENT DOCUMENTS

| | | | | | |
|---|---|---|---|---|---|
| 2,574,767 | A | * | 11/1951 | Stubbs | 128/834 |
| 3,442,266 | A | * | 5/1969 | Krejci et al. | 128/839 |
| 3,545,439 | A | * | 12/1970 | Duncan | 128/832 |

(Continued)

*Primary Examiner* — Oren Ginsberg
*Assistant Examiner* — Joshua Lee
(74) *Attorney, Agent, or Firm* — Lyman Smith; Kenneth Bower

(57) ABSTRACT

Disclosed is an intra-vaginal device of a new and innovative design that in combination with kegel exercises or performing ones daily routine strengthens the muscles of the pelvic floor. The device employs a combination of unique shape, materials as well as carefully engineered deflection, frictional, testing and clean-ability characteristics with particular attention to a sexually neutral appearance, comfort during insertion and exercise as well as positive physical feedback to encourage prolonged and frequent use. Benefits of the device include improvement or prevention of urinary leakage and prolapse, increases in sexual intensity, to keep the uterus, bladder or rectum in place as a pessary as well as relief for women suffering from moderate prolapse. As a dilator to aid women who suffer from vaginismus. With its multiple features and benefits, the device is a vital tool in a woman's quest for a complete and balanced wellness regimen.

25 Claims, 9 Drawing Sheets

(51) Int. Cl.
*A63B 23/20* (2006.01)
*A63B 21/055* (2006.01)

(56) References Cited

U.S. PATENT DOCUMENTS

| | | | | |
|---|---|---|---|---|
| 4,286,587 | A * | 9/1981 | Wong | 128/832 |
| 4,823,814 | A * | 4/1989 | Drogendijk et al. | 128/834 |
| 5,228,456 | A * | 7/1993 | Karg et al. | 128/837 |
| 5,342,273 | A * | 8/1994 | Plendl et al. | 482/126 |
| 5,695,444 | A * | 12/1997 | Chaney | 600/38 |
| 5,771,899 | A * | 6/1998 | Martelly et al. | 128/830 |
| 6,068,581 | A | 5/2000 | Anderson | |
| 6,158,435 | A * | 12/2000 | Dorsey | 128/830 |
| 6,216,698 | B1 * | 4/2001 | Regula | 128/830 |
| D458,681 | S | 6/2002 | Sherlock et al. | |
| 6,562,018 | B1 | 5/2003 | Russell | |
| 6,733,427 | B1 * | 5/2004 | He | 482/122 |
| 6,770,025 | B2 * | 8/2004 | Zunker | 600/29 |
| 7,686,747 | B1 | 3/2010 | Blackford | |
| D623,293 | S * | 9/2010 | Horsley | D24/141 |
| D623,393 | S * | 9/2010 | You | D3/5 |
| 7,910,126 | B2 * | 3/2011 | Ahmed et al. | 424/430 |
| 8,012,202 | B2 * | 9/2011 | Alameddine | 623/2.36 |
| 2003/0087734 | A1 | 5/2003 | Krig et al. | |
| 2003/0092963 | A1 * | 5/2003 | Yasue | 600/38 |
| 2004/0084054 | A1 * | 5/2004 | Kaseki et al. | 128/885 |
| 2007/0203429 | A1 * | 8/2007 | Ziv | 600/573 |
| 2009/0266367 | A1 * | 10/2009 | Ziv et al. | 128/834 |
| 2010/0010292 | A1 * | 1/2010 | Talbot et al. | 600/38 |
| 2010/0152844 | A1 * | 6/2010 | Couetil | 623/2.36 |
| 2011/0238171 | A1 * | 9/2011 | Carpentier et al. | 623/2.36 |
| 2012/0071709 | A1 * | 3/2012 | Spitz et al. | 600/30 |
| 2013/0005543 | A1 * | 1/2013 | Armitage et al. | 482/131 |
| 2013/0150661 | A1 * | 6/2013 | Rosen et al. | 600/29 |

* cited by examiner

Section A-A

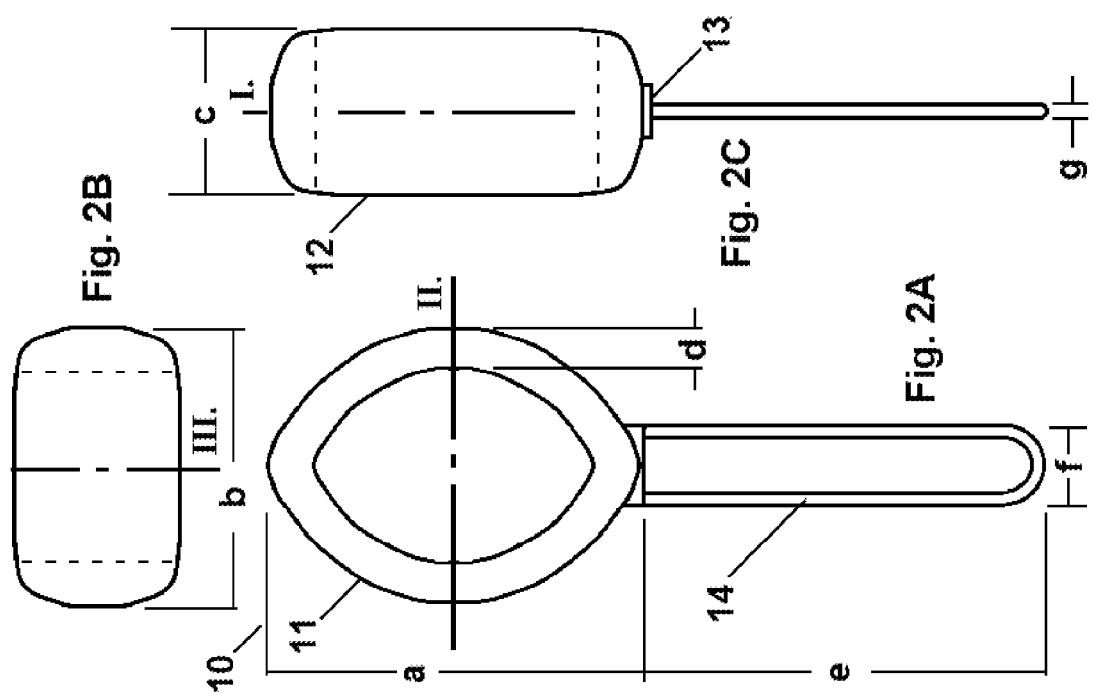

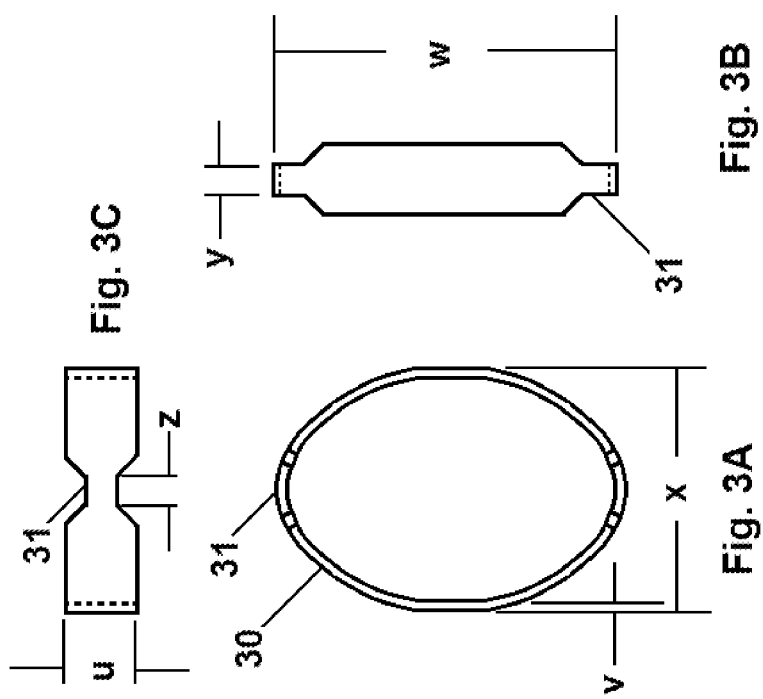

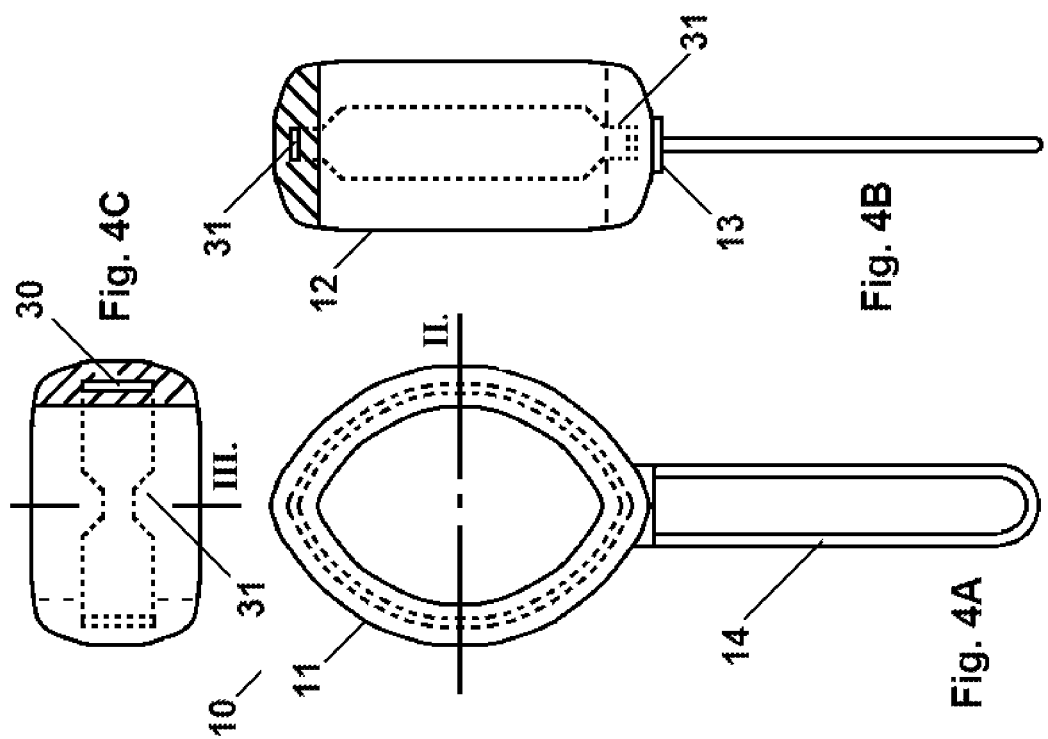

MEDICAL EXERCISE DEVICE

CROSS-REFERENCE TO RELATED APPLICATIONS

Not Applicable

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO SEQUENCE LISTING, A TABLE, OR A COMPUTER PROGRAM LISTING APPENDIX SUBMITTED ON A COMPACT DISC AND AN INCORPORATION-BY-REFERENCE OF THE MATERIAL ON THE COMPACT DISC

Not Applicable

BACKGROUND OF THE INVENTION

The present invention is a well-designed and effective kegel exercise device to strengthen a woman's pelvic muscles and aid in the prevention and reversal of incontinence. Ergonomically engineered to reinvigorate the pelvic floor, this portable intra-vaginal resistive product is compact, easy to use, and meets the needs of today's women regardless of age and active lifestyle demands.

The present invention is comprised of soft, pliable medical grade materials approved for short term implant applications. Its sleek precision engineered body also provides tactile feedback and progressive resistance to strengthen and tone the vaginal sphincter muscles when doing kegel exercises.

The limitations of kegel exercise devices in the prior art are that most involve multiple mechanical parts such as tubes, gauges, weights, balls, are cumbersome, and protrude partially outside the body. Add to the discomfort factor the inconvenience of needing to allocate specific times and private spaces to use them.

The present invention advances the state of the art with a one piece, unobtrusive, comfortable, lightweight, easy to insert, remove and clean product. This revolutionary discreet creation can be worn anywhere and at any time during the course of a woman's multi-tasking daily routine. In addition, with its unique combination of physical and mechanical properties, the present invention is more than a kegel muscle locator and motivator. It can be used: as an exercise device to help improve/prevent urinary leakage and prolapse, and increase sexual intensity; as a pessary to keep the uterus/bladder/rectum in place for women suffering from moderate prolapse. As a dilator to aid women who suffer from vaginismus. With its multiple features and benefits, the present invention is a vital tool in a woman's quest for a complete and balanced wellness regimen.

As a result, women can now take care of themselves from the inside out on their own terms because:

20 million women in the US are affected by urinary incontinence.

Notwithstanding underlying medical conditions, incontinence is not inevitable or part of the aging process because evidence exists that incontinence can be prevented and even reversed.

13 million women affected by urinary incontinence do not use any treatment or product to manage their condition.

1 in 4 women over the age of 50 suffer from prolapse.

BRIEF SUMMARY OF THE INVENTION

The preferred embodiment of the present invention is a soft, light weight, inconspicuous, comfortable, portable, intra-vaginal device with a sleek, sexually neutral, sculptured appearance that strengthens the pelvic floor, pubbococcygeal muscles, of the vagina. The device appears to be of simple design yet fulfills a number of interrelated requirements to facilitate ease of insertion, flexibility, resistance to multidirectional forces during use, providing pleasant feed back to the user and ease of removal. Additional requirements include ease of cleaning and durability for repeated use. Insertion and removal are facilitated by the device's prolate (football like) outline where the smaller width at the two ends is first to enter and exit the vaginal opening. The opening in the center of the prolate ring allows the ring to collapse further reducing resistance to entry and exit. There is also a finger pad to keep ones finger from slipping off of the ring while pushing the ring into place and a tension element that comfortably protrudes from the vaginal opening during use and aids in the removal of the device when use is completed. With the exception of the small exception of the small variation due to the finger pad the shape of the end of the prolate ring that enters the vagina first and the end that exits the vagina first are the same. The effectiveness of treatment with the device is enhanced by use of a well-known Kegel exercise routine in addition to leaving the device in place during every day activities and during conventional exercise.

It is the principal objective of the preferred embodiment of the present invention is to provide effective relief from incontinence, and pelvic organ prolapse, provide dilation for vaginismus, promote relaxation of vaginal muscles and to increase sexual intensity;

Another objective is to provide calibrated resistance to critical musculature keeping organs in their youthful positions and functioning in a reliable manner;

Another objective is to provide pleasant feedback to the user that motivates frequent and prolonged use;

Another objective is to present a neutral appearance that neither upsets the sensibilities of the user during handling, is not obtrusive during use, nor does it present the potential of an embarrassment in the eyes of others;

Another objective is to provide comfort during insertion, use and removal;

Another objective is ease of cleaning and durability for repeated use;

Another objective is effectiveness without the use of weights;

Basically the present invention allows women to accomplish all of these objectives with the confidence and freedom from discomfort and pain of a much younger person, without anyone knowing and while going about their daily lives.

BRIEF DESCRIPTION OF THE SEVERAL VIEWS OF THE DRAWINGS

FIG. 2A, shows a front view, FIG. 2B shows a top view and FIG. 2C shows aside view of the preferred embodiment of the present invention;

FIG. 3A, shows a front view, FIG. 3B shows a top and FIG. 3C shows a side view of the prolate shaped spring of the preferred embodiment of the present invention;

FIG. 4A, shows a front view, FIG. 4B shows a top and FIG. 4C shows a side view of the prolate shaped spring embedded in preferred embodiment of the present invention;

DETAILED DESCRIPTION OF THE PREFERRED EMBODIMENT

Figures 1A, 1B:
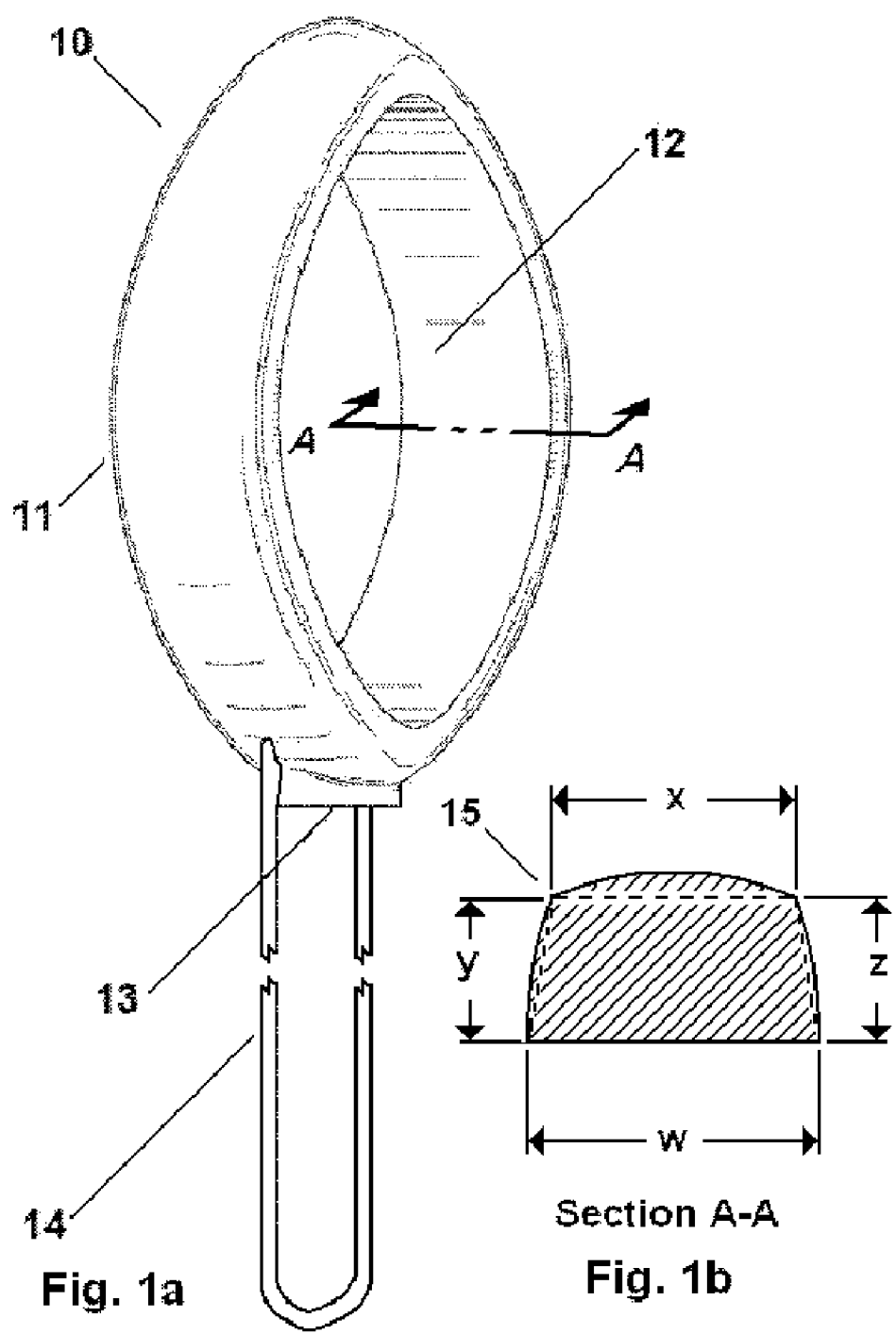
FIG. 1A, shows a perspective view of the preferred embodiment of the present invention.
FIG. 1B, shows a cross section of the view of FIG. 1A.

FIG. 1a shows the preferred embodiment of the present invention 10 which is specifically designed for inter-uterine application by human females. The preferred embodiment with its unusual shape is being described as a prolate ring 11. The term prolate is generally used to describe a family of solid geometrical shapes that includes the shape of an American football. The shape, elasticity, hysteresis characteristics, strength, frictional characteristics and weight all play an important part in delivering the two major measures of a successful device. These parameters are measures of the predicted effectiveness at overcoming a number of ailments including but not limited to effective relief from incontinence, and pelvic organ prolapse, promoting dilation for vaginismus, promoting relaxation of vaginal muscles and to increase sexual intensity and secondly providing comfort while doing so. The prolate shaped ring 11 is continuous without interruption and is symmetrical about the minor axis "II.", except for very small exceptions at the base, making the ease of insertion and the ease of extraction approximately equal.

Figure 6:
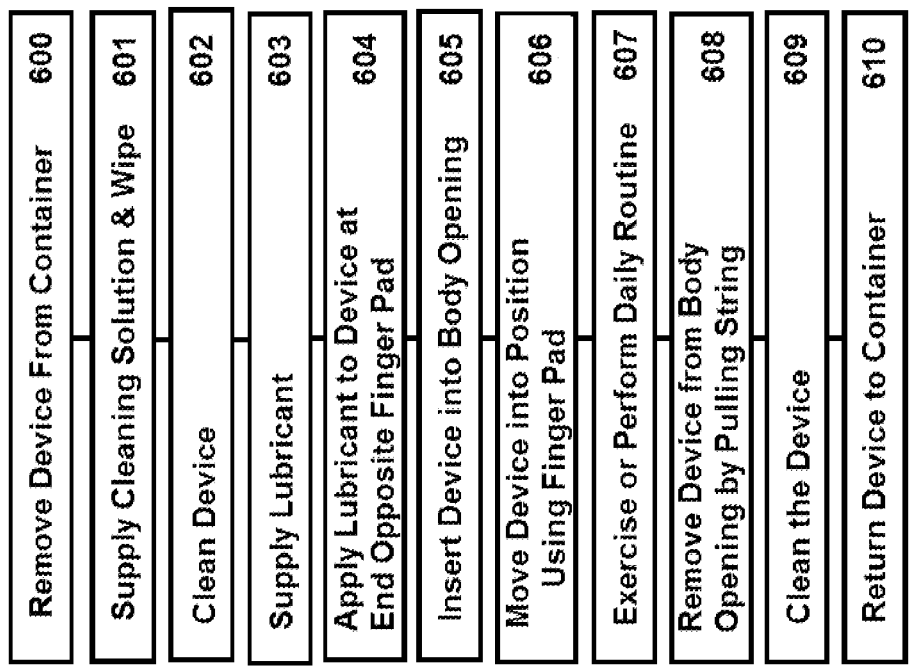
FIG. 6, is a block diagram showing the steps for using the preferred embodiment of the present invention.

The unobstructed, through opening 12 in the center of the prolate ring 11 plays an important role during steps 605, 606 and 608 of the method of use shown in FIG. 6. The opening 12 allows the prolate ring 11 to collapse during insertion 605 and to spring back into its original shape after insertion 606 is completed. There is provided a finger pad 13 at the intersection of the outer periphery of the prolate ring 11 and the major axis "I." that is a very slight protrusion from the prolate ring 11 with a flat or concave surface to provide traction with the tip of a user's finger while coaxing the prolate ring 11 into the bodily orifice during insertion. The long dimension of the surface of the finger pad 13 is approximately the width of a fingertip and less than half the thickness dimension of the prolate ring 11 while the center of the finger pad lies very close to a line that represents the outline of the outer periphery of the prolate ring. Tension element 14, otherwise referred to as a string, plays an important part in removing the prolate ring 11 from the bodily orifice 608 and transmits the force of extraction from the users hand to the prolate ring 11 while the prolate ring 11 collapses with the help of the unobstructed opening 12. The tension element 14 is only used for extraction as it is too thin and flexible to transmit a compressive force. The tension element 14 is also integral in one piece with the prolate shaped ring 11 and attaches at two points on either side of the finger pad 13.

FIG. 1b shows a cross section "A-" of the prolate shaped ring 10 that approximates the shape of an isosceles trapezoid 15 the short parallel side "x" of the isosceles trapezoid 15 forms part of a outer periphery of the prolate shaped ring 10. The long parallel side "w" of the isosceles trapezoid 15 forms a part of an inner periphery of the prolate shaped ring 10. The sloped sides "y" and "Z" of the isosceles trapezoid 15 are convexly curved. The short parallel side "x" of the isosceles trapezoid 15 is also convexly curved. The cross section of the prolate ring 10 promotes ease of insertion and extraction of the prolate ring 10 as well as comfort while the prolate ring 10 is in use.

FIG. 2, shows the preferred embodiment of the present invention 10 in three views. Prolate ring 11 has a opening 12 a finger pad 13 and tension element 14. The prolate ring 11 has a major diameter "a" that is taken along the major axis "I.", a minor diameter "b" that is taken along the minor axis "II." and a thickness measurement "c" that is taken along the axis "III." of the opening 12. The prolate ring 11 also has a hoop thickness "d", a tension element length "e" a tension element thickness of "g" and a tension element spacing of "f". The second column of Chart 1 shows the dimensions of the prolate ring 11 in millimeters. The third to twelfth columns show the dimensions of the prolate ring 11 in millimeters to possibly adapt the preferred embodiment for users having larger or smaller body sizes.

From CHART 1 it is observed that the minor diameter of the prolate ring ring "b" is between 63%-77% of the Major Diameter "a" of the prolate ring 1i. The thickness of the prolate ring "c" is between 36% and 45% of the Major Diameter "a" of the prolate ring 11. The hoop thickness of the prolate ring "c" is between 10% and 12% of the Major Diameter "a" of the prolate ring 11.

CHART 1

|  | Preferred Embodiment | 0.5 | 0.6 | 0.7 | 0.8 | 0.9 | 1.0 | 1.1 | 1.2 | 1.3 | 1.4 | 1.5 |
| --- | --- | --- | --- | --- | --- | --- | --- | --- | --- | --- | --- | --- |
| "a" | 71.87 | 50% | 60% | 70% | 80% | 90% | 100% | 110% | 120% | 130% | 140% | 150% |
| "b" | 50.26 | 35% | 42% | 49% | 56% | 63% | 70% | 77% | 84% | 91% | 98% | 105% |
| "c" | 29.14 | 20% | 24% | 28% | 32% | 36% | 41% | 45% | 49% | 53% | 57% | 61% |
| "d" | 8.16 | 6% | 7% | 8% | 9% | 10% | 11% | 12% | 14% | 15% | 16% | 17% |
| "e" | 92.83 | 65% | 77% | 90% | 103 | 116 | 129% | 142% | 155% | 168% | 181% | 194% |
| "f" | 14.59 | 10% | 12% | 14% | 16% | 18% | 20% | 22% | 24% | 26% | 28% | 30% |
| "g" | 2.81 | 2% | 2% | 3% | 3% | 4% | 4% | 4% | 5% | 5% | 5% | 6% |

FIG. 3, Shows a prolate shaped spring 30 that will be shown embedded in the prolate ring 11 in FIG. 4. Prolate shaped spring 30 is a flat spring (has a rectangular cross section) FIG. 3 has a notch 31 at two points in its periphery located at the tips of its prolate shape. Prolate shaped spring 30 has a major diameter "w", a minor diameter "x", a thickness measurement "u" and a hoop thickness "v". The notch 31 has a notch length "y" and a notch width "z". The second column of Chart 2 shows the dimensions of the prolate spring 30 in millimeters. The third to twelfth columns show the dimensions of the prolate spring 30 in millimeters to possibly adaptation to different body sizes. From CHART 2 it is observed that the minor diameter of the spring "x" is between 55%-67% of the Major Diameter "a" of the prolate ring 11.

CHART 2

|  | Preferred Embodiment | 0.5 | 0.6 | 0.7 | 0.8 | 0.9 | 1.0 | 1.1 | 1.2 | 1.3 | 1.4 | 1.5 |
|---|---|---|---|---|---|---|---|---|---|---|---|---|
| "w" | 60.81 | 42% | 51% | 59% | 68% | 76% | 85% | 93% | 102 | 110 | 118 | 127 |
| "x" | 43.56 | 30% | 36% | 42% | 48% | 55% | 61% | 67% | 73% | 79% | 85% | 91% |
| "u" | 10.19 | 7% | 9% | 10% | 11% | 13% | 14% | 16% | 17% | 18% | 20% | 21% |
| "v" | 1.64 | 1% | 1% | 2% | 2% | 2% | 2% | 3% | 3% | 3% | 3% | 3% |
| "y" | 2.67 | 2% | 2% | 3% | 3% | 3% | 4% | 4% | 4% | 5% | 5% | 6% |
| "z" | 1.77 | 1% | 1% | 2% | 2% | 2% | 2% | 3% | 3% | 3% | 3% | 4% |

FIG. 4, shows the preferred embodiment of the present invention 10 with a cut away view of prolate ring 11 and also having finger pad 13 and tension element 13. Spring 30 is shown suspended in the prolate ring 11 so that it is equidistant from the outer surface of the opening 12 and equidistant from the sides 32 of the prolate ring 11.

Figure 5:
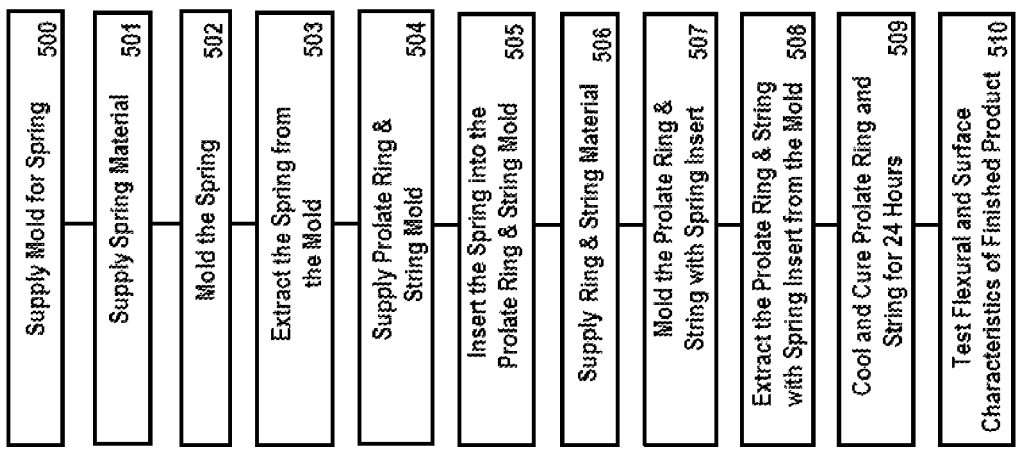
FIG. 5, is a block diagram showing the process steps for making the preferred embodiment of the present invention.

FIG. 5, shows the method of making the preferred embodiment of the present invention. The preferred embodiment 10 and the spring 30 each require a mold for manufacture. Step 500 calls for molding. There are any number of molding methods, processes and machines that can be adapted to manufacture the spring and over-mold to manufacture a finished device. It is considered that it is within the skill of one of ordinary skill to choose or design the mold, process and or machinery. Some of these methods, processes or machinery may also leave molding flash or gates on the prolate shaped spring 30 or over-mold after removal from the mold. Although, the block diagram of FIG. 5 does not include these process steps it is assumed to be within the skill of one of ordinary skill in the art to choose and or design the requisite ancillary tooling to trim and perform secondary process that are necessitated by the molding processes that are chosen. Step 501, requires supply of molding material. The preferred embodiment of the present invention uses polycarbonate resin as the molding material and the shape and thickness of the prolate shaped spring 30 are designed to produce resilience of the prolate ring to collapse for insertion into the vaginal opening during insertion as well as providing the required resistance to motion for strengthening pelvic floor muscles during exercise as described in FIG. 7. Step 502 is to mold the prolate shaped spring 30 followed by step 503 to remove the prolate shaped spring 30 from the prolate shaped spring 30 mold. Step 504 is to supply the prolate ring and tension element mold which has provisions to suspend the prolate shaped spring 30 to allow molding material to flow completely around the prolate shaped spring 30 to form the finished device of FIG. 1a. Step 505 is to insert the prolate shaped spring 30 into the prolate ring and tension element mold followed by step 506 to supply the ring and tension element material. The preferred embodiment of the present invention uses a medical grade silicone as the molding material. Step 507, is to mold the prolate ring and tension element, followed by step 508 to extract the prolate ring and tension element from the mold and step 509 to cool and cure the prolate ring and tension element for 24 hours before step 210 to test the flexural and surface characteristics of the finished device of FIG. 1a. The testing is performed to verify the device meets the resiliency for proper operation as listed in Chart 3.

CHART 3

| Direction of force applied to the device | Low end of range | High end of range |
|---|---|---|
| Compressive Down Major Axis | .5 mm/Newton | 2 mm/Newton |
| Compressive Down Minor Axis | .5 mm/Newton | 2 mm/Newton |
| Compressive Down Axis of Opening | .1 mm/Newton | .5 mm/Newton |
| Bending along Major Axis | .02 mm/Newton | .1 mm/Newton |

FIG. 6 shows the method of using the preferred embodiment of the present invention by females. The major difference in the method for the following uses is the period of time that the device remains in the vagina and whether or not exercising is performed while the device remains in the vagina. These differences are illustrated in Chart 4.

CHART 4.

|  | Used With Exercise | One Day or Less | Extended Periods Possible |
|---|---|---|---|
| Medical Exercise Device | X |  | X |
| Non-implant Pessary Device |  | X | X |
| Dilator to Relieve Vaginismus |  | X | X |
| Aid for Heightening Sexual Pleasure | X | X | X |

The steps of FIG. 6 are: Step 600, remove the device from container. The container serves to keep the device clean and physically protected. Cleanliness is mandatory for the good health of the user and the tension element is the most vulnerable part of the device to damage when carried in a pocket or purse. The container that is initially envisioned is a plastic travel box. However, there are any number of containers that would provide the requisite cleanliness and physical protection. The container is considered an accessory that would be within the skill of one of ordinary skill in the art to design or choose. Step 601, supply cleaning solution. The cleaning solution removes any body fluids, odors and sloughed off dead cells from the vaginal area. Soapy water or 70% by volume isopropyl alcohol has been found to be effective. Step 602 clean the device, is performed by a combination of applying cleaning solution with or without a wipe, optionally rinsing off the cleaning solution from the device and either wiping or allowing the device to air dry. Step 603 Supply Lubricant, any water based personal lubricant has been found to be effective as a lubricant to allow insertion of the device through the vaginal opening and into position for optimum use with a minimum of force and discomfort. Step 604, apply lubricant to device at end opposite the finger pad is achieved by dispensing a drop of the supplied lubricant in the specified location. The cleaning solution, any wipe or rinse material and lubricant are considered a depreciable supply items for device users that would be within the skill of one of ordinary skill in the art to design or choose for use either with or without wipe and rinse materials. Step 605, Insert device into body opening is achieved by positioning the device with the lubricated end entering first, flat sides of the device oriented vertically pinching the sides together and pushing the device with ones finger on the finger pad. Step 606 moving the device into position using the finger pad. This is done until the device is in a comfortable position within the vagina and the tension element protrudes from the vaginal opening. Step 607, exercise or perform daily routine is performed according to Chart 1, depending on the results that the user wants to achieve. Step 608, remove device from body opening by pulling on tension element is self-explanatory. One should adjust the force and speed of performing this step to minimize discomfort or any damage to sensitive tissues. Step 609, Clean the device is performed in the same manner as in step 602 except it is assumed that the device requires more cleaning and possibly repeating the procedure of step 602 multiple times to achieve the requisite cleanliness. Step 610 return device to container is perhaps the simplest yet most critical step.

Figure 7:
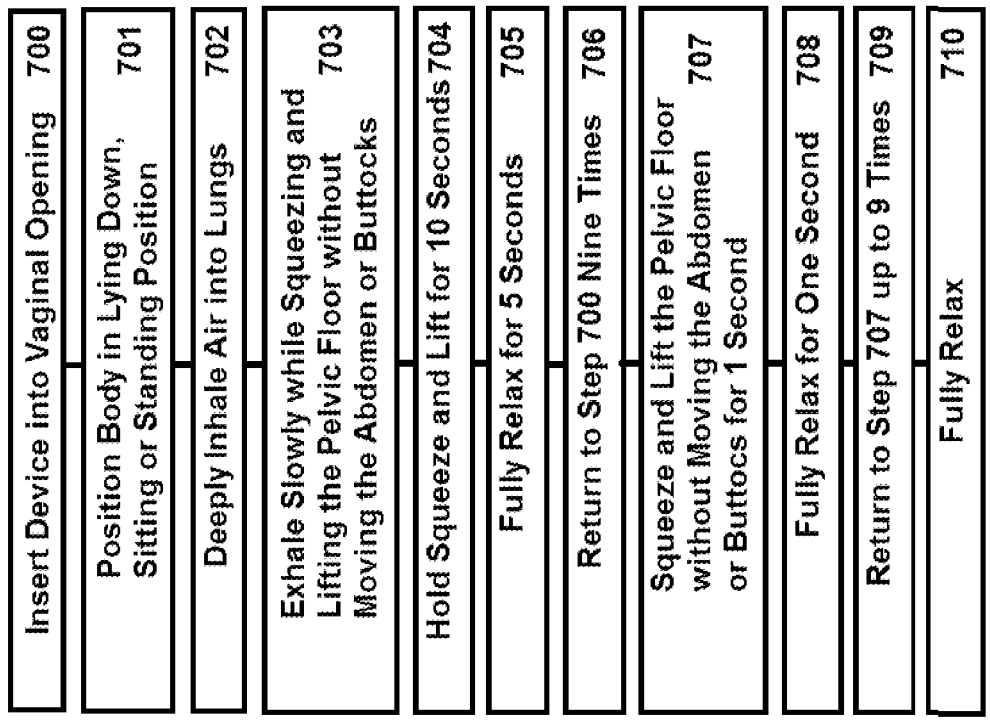
FIG. 7, is a block diagram showing the steps for Kegel exercising with the preferred embodiment of the present invention.

FIG. 7 shows the recommended steps for performing the Kegel exercise for use with the preferred embodiment of the present invention. Step 700 of the exercise involves following steps 600-610 of FIG. 6 to insert the device into the vaginal opening followed by step 701 to position the body in a lying down, sitting or standing position, followed by step 702 to deeply inhaling air into the lungs, and step 703 to exhale slowly while squeezing and lifting the pelvic floor without moving the abdomen or buttocks, followed by step 704 to hold the position of step 703 for 10 seconds, and step 705 to fully relax for 5 seconds. The sequence of steps 700 to step 705 is repeated a total of 10 times in step 706. The user then begins the much more rapid sequence of step 707 squeezing and lifting the pelvic floor without moving the abdomen or buttocks for one second, followed by step 708 to fully relax for 1 second and repeating the sequence step 707 and 708 a total of 10 times ending with fully relaxing at step 710. The coordinated breathing in and out are key to the successful outcome of performing these exercises.

Figure 8B:
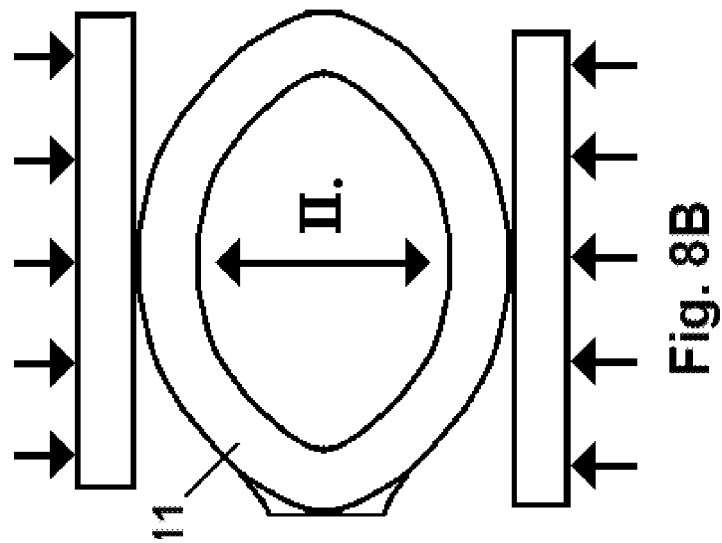
FIGS. 8A, 8B, 8C, and 8D, is a diagram are diagrams showing the application of forces to measure the deflection characteristics of the preferred embodiment of the present invention.
Figure 8A:
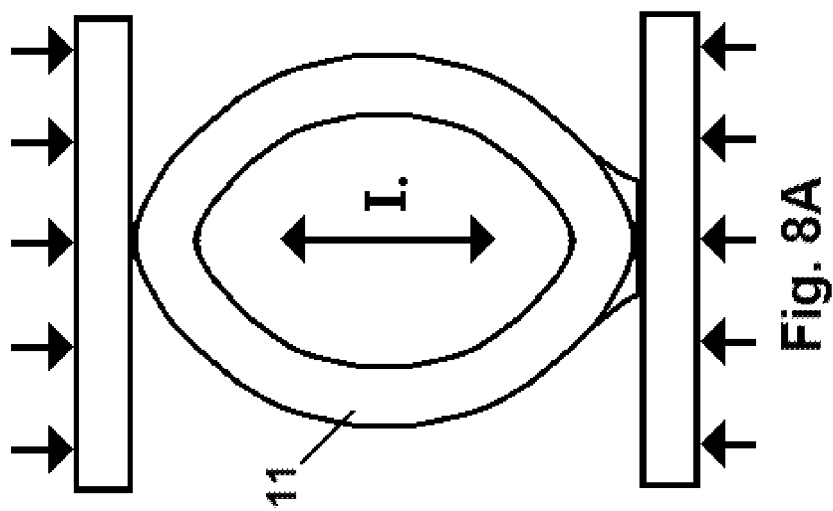
Figure 8D:
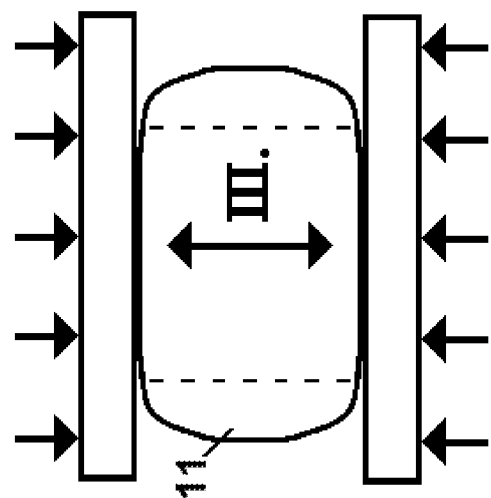
Figure 8C:
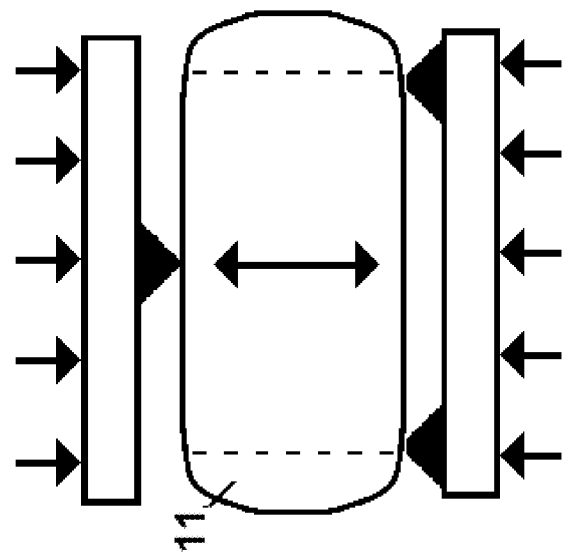

FIGS. 8a-8d, show the test set up for determining the deflection of the prolate ring 11 with forces applied. FIG. 8a, shows a compressive force in the direction of the major axis "I." of the prolate ring 11. FIG. 8b, shows a compressive force in the direction of the minor axis "II." of the prolate ring 11. FIG. 8c, shows a compressive force in the direction of the opening axis "III." of the prolate ring 11. FIG. 8d shows a bending force applied so as to bend the major axis "I." of the prolate ring 11.

I claim:
1. A medical exercise device comprising:
a prolate ring having a major axis and a minor axis;
one or more tension elements attached to the prolate ring in a proximity of an intersection of an outer periphery of the ring with said major axis;
a finger pad for increasing a traction with a finger;
a prolate shaped spring embedded in the prolate ring, the prolate shaped spring having a flattened shape, the prolate shaped spring having a width defined as being across the flattened shape generally perpendicular to the major axis and the minor axis; and
a notch formed in the prolate shaped spring, the notch disposed at the proximity of the intersection of the prolate ring with the major axis, the notch formed by notching opposite sides of the prolate shaped spring, across the width thereof;
wherein said prolate ring is continuous and symmetrical about said major axis and about said minor axis.
2. The medical exercise device of claim 1, wherein:
the prolate ring has an unobstructed through opening.
3. The medical exercise device of claim 1, wherein:
the one or more tension elements have a flexibility sufficient to transmit only tension forces.
4. The medical exercise device of claim 1, wherein:
a center of the finger pad intersects a continuation of an outer surface outline of the prolate ring and wherein a long dimension of a finger pad width is less than half the width of the prolate ring.
5. The medical exercise device of claim 1 wherein:
a cross section of the prolate ring, taken perpendicularly to a plane containing said major and minor axes, has an outline of essentially a shape of an isosceles trapezoid.
6. The medical exercise device of claim 5, wherein:
a short parallel side of the isosceles trapezoid forms a part of an outer circumference of the prolate ring;
a long parallel side of the isosceles trapezoid forms a part of an inner circumference of the prolate ring;
each of two sloped sides of the isosceles trapezoid are convexly curved;
and the short parallel side of the isosceles trapezoid is convexly curved.
7. The medical exercise device of claim 1, wherein:
a material of the prolate ring is silicone.
8. The medical exercise device of claim 1, wherein:
the prolate ring and the one or more tension elements are integral in one piece.
9. The medical exercise device of claim 1, wherein:
the prolate shaped spring has an essentially rectangular cross-section.
10. The medical exercise device of claim 1, wherein:
the prolate shaped spring deflects a first amount when subjected to a first compressive force applied parallel to the major axis;
the prolate shaped spring deflects a second amount when subjected to a second compressive force, equal to the first compressive force, applied parallel to the minor axis;
the second amount is greater than the first amount.
11. The medical exercise device of claim 1, wherein:
a material of the prolate shaped spring is a polymer resin.
12. The medical exercise device of claim 1, wherein:
a material of the prolate shaped spring is polycarbonate.
13. The medical exercise device of claim 1, wherein:
a diameter measured at the minor axis of the prolate ring is between 63% and 77% of a diameter measured at the major axis of the prolate ring.

14. The medical exercise device of claim 1, wherein:
a thickness of the prolate ring is between 36% and 45% of a major diameter of the prolate ring.

15. The medical exercise device of claim 1, wherein:
a hoop thickness of the prolate ring is between 10% and 12% of a major diameter of the prolate ring.

16. The medical exercise device of claim 1, wherein:
a deflection of the prolate ring resulting from a compressive force directed down the major axis of the prolate ring increases at a rate of 1 mm/Newton.

17. The medical exercise device of claim 1, wherein:
a deflection of the prolate ring resulting from a compressive force directed down the minor axis of the prolate ring increases at a rate of 1 mm/Newton.

18. The medical exercise device of claim 1, wherein:
a deflection of the prolate ring resulting from an evenly distributed load applied in the direction of an axis of the opening increases at a rate of 0.25 mm/Newton.

19. The medical exercise device of claim 1, wherein said notch has a length and a width adapted so as to provide a first predetermined resistance when subjected to a first compressive force and a second predetermined resistance when subjected to a second compressive force.

20. A medical exercise device comprising:
a prolate ring having a major axis and a minor axis;
one or more tension elements attached to the prolate ring in a proximity of an intersection of an outer periphery of the ring with said major axis;
a finger pad for increasing traction with a finger;
a prolate shaped spring embedded in the prolate ring, the prolate shaped spring having a width defined as being across the flattened shape generally perpendicular to the major axis and the minor axis; and
a notch formed in the prolate shaped spring, the notch disposed at the proximity of the intersection of the prolate ring with the major axis, the notch formed by notching opposite sides of the prolate shaped spring, across the width thereof, the prolate shaped spring being continuous about a central, widthwise circumference thereof;
wherein said prolate ring is continuous and symmetrical about said major axis and about said minor axis.

21. The medical exercise device of claim 20, wherein:
the prolate ring has an unobstructed through opening.

22. The medical exercise device of claim 20, wherein:
the prolate ring and the one or more tension elements are integral in one piece.

23. The medical exercise device of claim 20, wherein:
the prolate shaped spring deflects a first amount when subjected to a first compressive force applied parallel to the major axis;
the prolate shaped spring deflects a second amount when subjected to a second compressive force, equal to the first compressive force, applied parallel to the minor axis; and
the second amount is greater than the first amount.

24. A medical exercise device comprising:
a prolate ring having a major axis and a minor axis;
one or more tension elements attached to the prolate ring in a proximity of an intersection of an outer periphery of the ring with said major axis;
a finger pad for increasing traction with a finger;
a prolate shaped spring embedded in the prolate ring, the prolate shaped spring having a flattened shape, the prolate shaped spring having a width defined as being across the flattened shape generally Perpendicular to the major axis and the minor axis; and
a notch formed in the prolate shaped spring, the notch disposed at the proximity of the intersection of the prolate ring with the major axis, the notch formed by notching opposite sides of the prolate shaped spring, across the width thereof, wherein
the prolate ring has an unobstructed through opening;
the prolate shaped spring deflects a first amount when subjected to a first compressive force applied parallel to the major axis;
the prolate shaped spring deflects a second amount when subjected to a second compressive force, equal to the first compressive force, applied parallel to the minor axis; and
the second amount is greater than the first amount.

25. The medical exercise device of claim 24, wherein:
the prolate ring and the one or more tension elements are integral in one piece.

* * * * *